(12) United States Patent
Mourier-Robert et al.

(10) Patent No.: US 10,092,506 B2
(45) Date of Patent: *Oct. 9, 2018

(54) ENCAPSULATION OF LIPOPHILIC OR AMPHIPHILIC THERAPEUTIC AGENTS IN NANO-EMULSION

(75) Inventors: Veronique Mourier-Robert, Grenoble (FR); Jerome Bibette, Paris (FR); Mathieu Goutayer, Saint Malo (FR); Fabrice Navarro y Garcia, Grenoble (FR); Isabelle Texier-Nogues, Grenoble (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 13/058,850

(22) PCT Filed: Aug. 14, 2009

(86) PCT No.: PCT/EP2009/060539
§ 371 (c)(1),
(2), (4) Date: May 9, 2011

(87) PCT Pub. No.: WO2010/018223
PCT Pub. Date: Feb. 18, 2010

(65) Prior Publication Data
US 2011/0201695 A1    Aug. 18, 2011

(30) Foreign Application Priority Data
Aug. 14, 2008 (FR) ..................... 08 55589

(51) Int. Cl.
*A61K 9/00* (2006.01)
*A61K 47/69* (2017.01)
(Continued)

(52) U.S. Cl.
CPC .......... *A61K 9/0019* (2013.01); *A61K 9/1075* (2013.01); *A61K 41/0071* (2013.01); *A61K 47/6907* (2017.08); *B82Y 5/00* (2013.01)

(58) Field of Classification Search
CPC .............. A61K 9/0019; A61K 47/6907; A61K 41/0071; A61K 9/1075; B82Y 5/00
See application file for complete search history.

(56) References Cited

U.S. PATENT DOCUMENTS 4,906,100 A   3/1990 Rice et al.
5,098,606 A   3/1992 Nakajima et al.
(Continued)

FOREIGN PATENT DOCUMENTS

CN    1676125 A    10/2005
EP    0211258 A2    2/1987
(Continued)

OTHER PUBLICATIONS

"Nano-emulsion formulation using spontaneous emulsification: solvent, oil and surfactant optimization", by Bouchemal et al., International Journal of Pharmaceutics 280 (2004) 241-251.*
(Continued)

*Primary Examiner* — Trevor Love
(74) *Attorney, Agent, or Firm* — Westerman, Hattori, Daniels & Adrian, LLP

(57) ABSTRACT

The present invention relates to a therapeutic agent formulation in the form of a nano-emulsion, comprising a continuous aqueous phase and at least one dispersed oily phase, in which the oily phase comprises further to the therapeutic agent, at least one amphiphilic lipid and at least one solubilizing lipid, and in which the aqueous phase comprises at least one polyalkoxylated cosurfactant.

Figure 1:
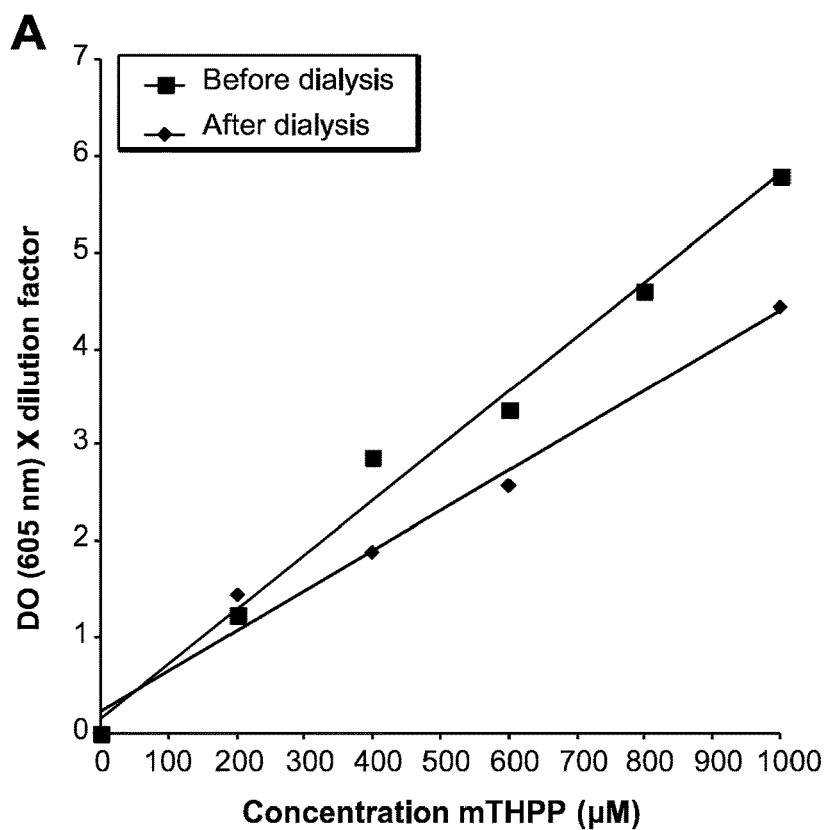
Figure 1:
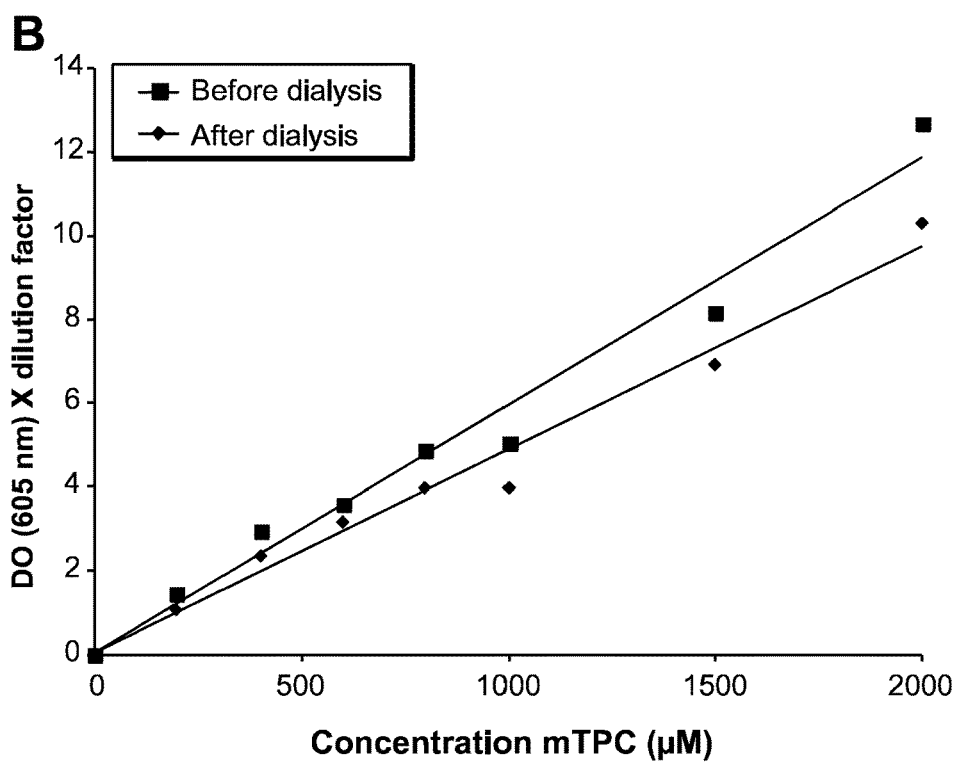

The invention also relates to a preparation method and use of this formulation.

13 Claims, 7 Drawing Sheets

(51) Int. Cl.
*A61K 41/00* (2006.01)
*A61K 9/107* (2006.01)
*B82Y 5/00* (2011.01)

(56) References Cited

U.S. PATENT DOCUMENTS

| | | |
|---|---|---|
| 5,152,923 A | 10/1992 | Weder et al. |
| 5,403,575 A | 4/1995 | Kaufman et al. |
| 5,464,696 A | 11/1995 | Tournier et al. |
| 5,472,706 A | 12/1995 | Friedman et al. |
| 5,665,687 A | 9/1997 | Khayat et al. |
| 5,976,502 A | 11/1999 | Khoobehi et al. |
| 6,113,921 A | 9/2000 | Friedman et al. |
| 6,123,923 A | 9/2000 | Unger et al. |
| 6,350,431 B1 | 2/2002 | Snow et al. |
| 6,541,018 B1 | 4/2003 | Simmonet et al. |
| 6,559,183 B1 | 5/2003 | Schmid et al. |
| 6,949,257 B2 | 9/2005 | Lang et al. |
| 7,014,839 B2 | 3/2006 | Klaveness et al. |
| 8,557,861 B2 | 10/2013 | Chen |
| 2002/0015721 A1* | 2/2002 | Simmonet et al. ......... 424/427 |
| 2002/0102301 A1 | 8/2002 | Schwarz |
| 2003/0157021 A1 | 8/2003 | Klaveness et al. |
| 2004/0092428 A1 | 5/2004 | Chen et al. |
| 2005/0079131 A1 | 4/2005 | Lanza et al. |
| 2005/0129639 A1 | 6/2005 | Quemin |
| 2005/0180997 A1 | 8/2005 | Benita et al. |
| 2005/0255044 A1 | 11/2005 | Lomnes et al. |
| 2006/0257493 A1 | 11/2006 | Amiji et al. |
| 2007/0053988 A1 | 3/2007 | Royere et al. |
| 2007/0092447 A1 | 4/2007 | Padilla de Jesus et al. |
| 2007/0148194 A1 | 6/2007 | Amiji et al. |
| 2009/0152635 A1 | 6/2009 | Jeong et al. |
| 2010/0144899 A1 | 6/2010 | Goutayer et al. |
| 2010/0284932 A1 | 11/2010 | Goutayer et al. |
| 2011/0195029 A1 | 8/2011 | Guyon et al. |
| 2011/0200532 A1 | 8/2011 | Goutayer et al. |
| 2011/0274622 A1 | 11/2011 | Texier-Nogues et al. |

FOREIGN PATENT DOCUMENTS

| | | |
|---|---|---|
| EP | 0406162 A | 1/1991 |
| EP | 0429248 A2 | 5/1991 |
| EP | 1010416 A | 6/2000 |
| EP | 1018363 A | 7/2000 |
| EP | 1693445 A1 | 8/2006 |
| GB | 2251381 A | 7/1992 |
| JP | 62-29511 A | 2/1987 |
| JP | 03-47527 A | 2/1991 |
| JP | 03-161430 A | 7/1991 |
| JP | 04-504108 A | 7/1992 |
| JP | 07-503976 A | 4/1995 |
| JP | 08-157325 A | 6/1996 |
| JP | 08-506081 A | 7/1996 |
| JP | 08-507515 A | 8/1996 |
| JP | 2001-519396 A | 10/2001 |
| JP | 2001-526650 A | 12/2001 |
| JP | 2006-008700 A | 1/2006 |
| JP | 2006-223306 A | 8/2006 |
| JP | 2008-514720 A | 5/2008 |
| WO | 90/06746 A1 | 6/1990 |
| WO | 93/18752 A1 | 9/1993 |
| WO | 94/04197 A1 | 3/1994 |
| WO | 94/20072 A1 | 9/1994 |
| WO | 9848845 A | 11/1998 |
| WO | 9857666 A | 12/1998 |
| WO | 99/18967 A1 | 4/1999 |
| WO | 00/28971 A1 | 5/2000 |
| WO | 01/64328 A | 9/2001 |
| WO | 93/12766 A1 | 7/2003 |
| WO | 2005077422 A2 | 8/2005 |
| WO | 2006/037089 A2 | 4/2006 |
| WO | 2006087156 A1 | 8/2006 |
| WO | 2006/102768 A1 | 10/2006 |
| WO | 2008102065 A1 | 8/2008 |
| WO | 2008125747 A2 | 10/2008 |
| WO | WO 2008128779 A1 * | 10/2008 |

OTHER PUBLICATIONS

Hsu et al. "Behavior of soybean oil-in-water emulsion stabilized by nonionic surfactant", Journal of Colloid and Interface Science, 259 (2003) 374-381.*

Heurtault et al., "Physico-chemical stability of colloidal lipid particles," Biomaterials, 24(2003):4283-4300.*

Weyenberg et al. "Cytotoxicity of submicron emulsions and solid lipid nanparticles for dermal application" ,International Journal of Pharmaceutics, 337 (2007) 291-298.*

Gattefosse: Suppocire AS2 Pellets, 2010.*

Kumar et al."Intranasal nanoemulsion based brain targeting drug delivery system of risperidone", International Journal of Pharmaceutics; 358 (2008) 285-291, Mar. 29, 2008.*

Liversidge et al., "Influence of physicochemical interactions on the properties of suppositories," International Journal of Pharmaceutics Elsevier, BV, NL, vol. 7, No. 3 (1991), cited in ISR, in English.

Primo et al.: "Binding and photophysical studies of biocompatibel magnetic fluid in biological medium and development of magnetic nanoemulsion: A new candidate for cancer treatment", Journal of Magnetism and Magnetic Materials, Elsevier Science Publishers, Amsterdam, NL, vol. 310, No. 2, pp. 2838-2840 (2007), cited in ISR.

Bourdon et al., "A comparative study of the cellular uptake, localization and phototoxicity of meta-tetra(hydroxyphenyl chlorin encapsulated in surface-modified submicronic oil/water carriers in HT29 tumor cells," Journal of Photochemistry and Photobiology, vol. 55, lines 2-3 (2000), cited in ISR, in English.

Bourdon et al., "Biodistribution of meta-tetra(hydroxyphenyl)chlorin incorproated into surface-modified nanocapsules in tumor-bearing mice," Photochemical and Photobiological Sciences, vol. 1, No. 9, pp. 709-714 (2002), cited in ISR, in English.

Primo et al., "Photophysical studies and in vitro skin permeation/retention of Foscan/nanoemulsion (NE) applicable to photodynamic therapy skin cancer treatment," Journal of Nanoscience and Nanotechnology, Vo. 8, No. 1, pp. 340-347 (2008), cited in ISR, in English.

Mordon et al., "Selective laser photocoagulation of blood vessels in a hamster skin flap model using a specific ICG formulation," Lasers in Surgery and Medicine, vol. 21, No. 4, pp. 365-373 (1997), cited in ISR, in English.

Chung et al., "Stability of the oil-in-water type triacylglycerol emulsions," Biotehnology and Bioprocess Engineering, vol. 6, pp. 284-288 (2001), cited in ISR, in English.

Reddi, "Role of delivery vehicles for photosensitizers in the photodynamic therapy of tumors," J. of Photochemistry and Photobiology, Biology, Elsevier Science, Basel, Switzerland, vol. 37, No. 3, pp. 189-195 (1997), cited in ISR, in English.

Mehnert et al., "Solid lipid nanoparticles production, characterization and applications," Advanced Drug Delivery Reviews, Elsevier BV, Amsterdam, Netherlands, vol. 47, No. 2/03, pp. 163-196 (2001), cited in ISR, in English.

International Search Report (ISR) in PCT/EP2009/060539 dated Dec. 22, 2009.

Jiang et al., "γtocopherol, the major form of vitamin E in the US diet, deserves more attention", Am. J. Clin. Nutr. 2001; 74:174-22; Cited in co-pending U.S. Appl. No. 12/527,371.

Rodriguez et al., "Encapsulation and stabilization of indocyanine green within poly(styrene-alt-maleic anhydride) block-poly(styrene) micelles for near-infrared imaging", J. Biomedical Optics, vol. 13, No. 1, pp. 014025-1 to 014025-10 (Jan.-Feb. 2008); Cited in Japanese counterpart of U.S. Appl. No. 13/058,850.

International Search Report (ISR) dated Jan. 22, 2009 for International Application No. PCT/FR2008/000196 (WO2008/125747A3), corres. to U.S. Appl. No. 12/527,314.

Kalchenko et al., "Use of lipophilic near-infrared dye in whole-body optical imaging of hematopoietic cell homing", J. of Biomedical

(56) References Cited

OTHER PUBLICATIONS

Optics, vol. 11, No. 5, Sep. 2006, p. 050507, XP002511213; Cited in ISR of co-pending U.S. Appl. No. 12/527,314.
Entry for "lecithin", Stedman's Medical Dictionary, 28th Ed., 2005 Lippincott Williams & Witkins; Cited in co-pending U.S. Appl. No. 12/527,314; Cited in co-pending U.S. Appl. No. 13/058,849; Cited in co-pending U.S. Appl. No. 13/058,851.
Suppocire, TM, Standard product information, 2010 Gattefosse website <http://www.gattefosse.com/en/applications/?administration-route.rectal-veginal.standards>, Accessed Aug. 9, 2012; Cited in co-pending U.S. Appl. No. 12/527,314; Cited in co-pending U.S. Appl. No. 13/058,849; in co-pending U.S. Appl. No. 13/058,851.
Friedlander et al., Involvement of integrins alpha v. beta 3 and alpha v. beta 5 in ocular neovasclar diseases, 1996 Proc. Natl Acad. Sci., USA 93:9764-9769; Cited in co-pending U.S. Appl. No. 12/527,314.
International Search Report (ISR) dated Dec. 22, 2009 for International Application No. PCT/FR2008/050249 (WO2008/104717A3), corres. to U.S. Appl. No. 12/527,371.
Zeevi et al., "The design and characterization of a positively charged submicron emulsion contianing a sunscreen agent", Intl. J. of Pharmaceutics, Elsevier BV, NL, vol. 108, No. 1 (Jan. 1, 1994), pp. 57-68, XP008013777; Cited in ISR of co-pending U.S. Appl. No. 12/527,371.
Mason et al., "Nanoemulsions: formation, structure and physical properties", J. Phys: Condens. Matter, vol. 18, Sep. 29, 2006, pp. R635-R665, XP002502173; Cited in ISR of co-pending U.S. Appl. No. 12/527,371.
International Search Report (ISR) dated Dec. 22, 2009 for International Application No. PCT/FR2009/060534 (WO2010/018222A1), corres. to U.S. Appl. No. 13/058,849.
Liu et al., "A new bioimaging carrier for fluorescent quantum dots: Phospholipid nanoemulsion mimicking natural lipoprotein core", Drug Delivery: Journal of Delivery and Targeting of Therapeutic Agents, vol. 13, No. 2, pp. 159-164 (2006); Cited in ISR of co-pending U.S. Appl. No. 13/058,849.
Anonymous, 2007 AAPS Annual Meeting & Exposition—Sasol Olefins & Surfactants Product Brochure, Nov. 10-15, 2007, http://abstracts.aapspharmaceutica.com/ExpoAAPS07/Data/EC/Event?Exhibitors/e62/cb63fb76-28f4-4948-a6d0-ae249dae9c30.pdf (retrieved Mar. 12, 2009), cited in ISR of co-pending U.S. Appl. No. 13/058,849.
Goutayer et al., "Organic Nano-Particles for Non-Invasive Fluorescence Imaging in Mice," Bulletin du Cancer (Montrouge), vol. 95, No. Sp. Iss. SI, pp. S21-S22 (2008); Cited in ISR of co-pending U.S. Appl. No. 13/058,849.
French search report (FSR) dated Mar. 12, 2009 for priority French Appl. No. 0855588 of co-pending U.S. Appl. No. 13/058,849 (w/ category codes).
Bai et al.: "A versatile bottom-up assembly approach to colloidal spheres from nanocrystals," Angewandte Chemie International Edition Wiley-Vch Verlag GmbH, Germany, vol. 46, No. 35, pp. 6650-6653 (2007); Cited in French search report of priority French Appl. No. 0855588 of co-pending U.S. Appl. No. 13/058,849.

Akkar et al.: "Formulation of intravenous Carbamazepine emulsions by SolEmuls<(>R) technology," European Journal of Pharmaceutics and Biopharmaceutics, Elsevier Science Publishers B.V., Amsterdam, The Netherlands, vol. 55, No. 3, pp. 305-312 (2003); Cited in French search report of priority French Appl. No. 0855588 of co-pending U.S. Appl. No. 13/058,849.
Anonymous: "Lipofundin MCT/LCT," B. Braun Melsungen AG Product Information, http://www.gheg.de/media/product/4623/Product_info.pdf (retrieved Mar. 12, 2009); Cited in French search report of priority French Appl. No. 0855588 of co-pending U.S. Appl. No. 13/058,849.
Liu et al., "Preparation and characterization of novel fluorescent nanocomposite particles: CdSe/ZnS core-shell quantum dots loaded solid lipid nanoparticles", J. of Biomedical Materials Research Part A, vol. 84, pp. 1018-1025 (pub. online Aug. 1, 2007); Cited in ISR in co-pending U.S. Appl. No. 13/058,849.
International Search Report (ISR) dated Apr. 20, 2010 for International Application No. PCT/EP2009/060518 (WO2010018216A1), corres. to co-pending U.S. Appl. No. 13/058,851.
Gunstone et al. "Lipid Technologies and Applications", CRC Press, Ed. 1, p. 672 (1997); Cited in ISR in co-pending U.S. Appl. No. 13/058,851.
International Search Report (ISR) dated Jan. 15, 2010 for International Application No. PCT/IB2009/006766 (WO2010/018460A1), corres. to U.S. Appl. No. 13/058,984.
Teixiera et al., "Factors Influencing the Oligonucleotides Release From O-W Submicron Cationic Emulsions". Journal of Controlled Release, Elsevier,vol. 70, No. 1/02, pp. 243-255, XP 001197324, ISSN: 0168-3659 (Jan. 29, 2001); Cited in ISR of co-pending U.S. Appl. No. 13/058,984; Cited in co-pending U.S. Appl. No. 13/058,984.
Teixeira et al., "Characterization of Oligonucleotide Lipid Interactions in Submicron Cationic Emulsions: Influence of The Cationic Lipid Structure and the Presence of PEG-Lipids", Biophysical Chemistry, vol. 92, No. 3. pp. 169-181, XP001197325, ISSN: 0301-4622, (Sep. 18, 2001); Cited in ISR of co-pending U.S. Appl. No. 13/058,984.
Chattopadhyay et al., "Chemistry and Biology of N-(7-nitrobenz-2-oxa-1,3-diazol-4-yl)-labeled lipids: Fluorescent Probes of Biological and Model Membranes", Review Article, Chemistry and Physics of Lipids, vol. 53, No. 1, pp. 1-15, XP024783533, ISSN: 0009-3084, (Mar. 1, 1990); Cited in ISR of co-pending U.S. Appl. No. 13/058,984.
Chen et al., "Fast Release of Lipophilic Agents From Circulating PEG-PDLLA Micelles Revealed by In Vivo Forster Resonance Energy Transfer Imaging", Langmuir, vol. 24, No. 10, pp. 5213-5217, XP002510881, ISSN: 0743-7463, (Aug. 2, 2008); Cited in ISR of co-pending U.S. Appl. No. 13/058,984.
Lundberg, "Preparation of drug-carrier emulsions stabilized with phosphatidylcholine-surfactant mixtures", J. Pharm. Sci., vol. 83, pp. 72-75 (1994); Cited in co-pending U.S. Appl. No. 12/527,314.
Office Action dated Apr. 13, 2016 in co-pending U.S. Appl. No. 12/527,371 (without returned SB08, total 23 pages).

\* cited by examiner

A

B

ENCAPSULATION OF LIPOPHILIC OR AMPHIPHILIC THERAPEUTIC AGENTS IN NANO-EMULSION

The present invention relates to a composition of the nano-emulsion type of use notably for delivering lipophilic or amphiphilic therapeutic agents, a method for preparing it as well for using it for the treatment and diagnosis of diseases, notably cancer.

JOINT RESEARCH AGREEMENT

This application is for a claimed invention which was made on or on behalf of parties to a Joint Research Agreement (JRA). The parties to the JRA are:
Commissariat à l'Energie Atomique et aux Energies Alternatives ("CEA"),
Centre National de la Recherche Scientifique ("CNRS"),
Université Pierre et Marie Curie ("Paris 6").

STATE OF THE ART

Nanomedicine constitutes a new field created by the fusion of nanotechnology and medicine and is at the present time one of the most promising routes for the development of effective targeted therapies, notably for oncology.

In point of fact, nanoparticles charged with therapeutic agents constitute an ideal solution for overcoming the low selectivity of medicines, notably anticancer medicines, by enabling cancerous tissues to be targeted, by means of passive and/or active targeting, and this is a way to reduce severe side effects.

A large variety of nanoparticles have been tested for therapeutic and imaging applications, both inorganic (for example semiconductors, silica or oxides) as well as organic (natural or synthetic polymers, liposomes, nanospheres, nanocapsules, microspheres).

It has been found that polymeric nanoparticles have potential cytotoxicity associated notably with residues of organic solvents, as well as production difficulties of reproducibility on a large scale and storage life problems. Liposomes are limited in terms of stability and degree of encapsulation of lipophilic compounds and their method of production is complex.

As an alternative to polymeric nanoparticles, attention has been focussed since 1990 on lipid nanoparticles comprising a lipidic core, more often based on biodegradable triglycerides, surrounded by a polymeric shell. The choice of biocompatible lipids, as well as the possibility of producing them without solvents, makes it possible to reduce notably their toxicity (Muller, R. H., Eur J Pharm Biopharm 2000, 50, 161-177; Mehnert, W., et al., Advanced Drug Delivery Reviews 2001, 47, 165-196). More often they consist of solid lipid particles (SLN, an acronym for "Solid Lipid Nanoparticles") in which the lipid core is solid at room temperature. They may also consist of emulsions, in which the nanoparticles are formed of a lipid phase dispersed in an aqueous solution and stabilised by surfactants.

However, the technology of SLNs still does not make it possible to control growth and there is an unforeseen tendency for gelation and unexpected dynamic polymorphic transitions. In addition, SLNs possess a limited capacity to be incorporated by the crystalline structure of the solid lipid (Mehnert, W., et al, Advanced Drug Delivery Reviews 2001, 47, 165-196; Westesen, K., et al. International Journal of Pharmaceutics 1997, 151, 35 45; Westesen, K., et al., Journal of Controlled Release 1997, 48, 223-236).

Document WO 01/64328 describes lipid nanocapsules consisting of a liquid or semi-liquid core surrounded by a solid shell with a thickness of a few nanometers that may encapsulate an active pharmaceutical ingredient. Nanocapsules are obtained by a thermal method in which the mixture of oily and aqueous components is submitted to temperature cycles (between 60 and 85° C.) around the phase inversion temperature (PIT) of the emulsion formed. The microemulsion obtained is then subjected to quenching by adding cold water.

This method requires specific equipment in order to detect the phase inversion of the emulsion and is incompatible with many therapeutic agents on account of the high temperature reached. In addition, the formation of a solid surface shell complicates the subsequent anchoring of biological targeting ligands. Moreover, quenching requires the addition of large volumes of cold water (3 to 10 times dilution) and therefore considerably reduces the yield of nanocapsules. In addition, the chemical nature of fatty acid triglycerides has a marked effect on the phase inversion temperature, which restricts their choice.

Document US 2006/0292186 describes an anhydrous auto-nano-emulsifying formulation for the administration of active ingredients which are poorly water-soluble such as paclitaxel. These formulations contain a high proportion of Tyloxapol and TPGS, synthetic polymeric surfactants.

Document WO 2008/042841 describes pre-concentrates of paclitaxel emulsion containing an anionic phospholipid. Dispersed in an aqueous phase, the formulation forms an oil-in-water emulsion of which the droplets carry a negative charge. These emulsions are, however, unstable and therefore have to be prepared just before administration.

In addition, Tarr et al, (1987) Pharm. Res. 4:162-165, report a formulation of paclitaxel in Intralipid, an emulsion for parenteral use, but the low solubility of paclitaxel in soybean oil (0.3 mg/ml) makes this excipient unsuitable.

The effective administration of therapeutic agents of the photosensitizer type also constitutes a considerable challenge in photodynamic therapy, which is a promising technique for treating various cancers. The principle of this technique is based on the introduction of a photosensitizer into the tumour tissue and conversion of this therapeutic agent with the aid of light radiation of a suitable wavelength into a highly cytotoxic compound. It has been postulated that the cytotoxic effect of photosensitizers is due to the formation of singlet oxygen after light irradiation.

The selectivity of this method depends on the selective accumulation of the photosensitizer in tumour tissue as against healthy tissues and more particularly within the actual tumour cells. At the present time, the low tumour selectivity of the agents after they are systemically injected produces, for patients, a prolonged period of cutaneous photosensitivity of at least 6 to 8 weeks.

Perfecting administration systems for photosensitizers therefore also constitutes an important challenge for the development of photo-dynamic therapy.

Document WO 00/28971 describes formulations for the topical administration of 5-aminolaevulinic acid (5-ALA) for phototherapy and diagnostics containing a nano-emulsion.

Finally, in order to reduce the period of cutaneous photosensitivity, document US 2005/0215524 proposes the administration of an emulsion of phospholipids before, during or after photo-therapeutic treatment by photosensitizers. In the examples, the photosensitizer is directly solubilized in the injected phospholipids, which promotes its rapid clearance in the plasma and in the skin.

TECHNICAL PROBLEM

The formulation of high doses of lipophilic and amphiphilic therapeutic agents in stable nano-emulsions enabling effective targeted delivery therefore remains a challenge.

In the present invention we propose a formulation in which the therapeutic agent is encapsulated in a nano-emulsion having an oily phase with a specific composition.

SUMMARY OF THE INVENTION

The present invention describes a novel formulation of therapeutic agents by encapsulation in an oil-in-water nano-emulsion.

By virtue of a specific formulation, the nano-emulsion according to the invention is stable and makes it possible to reach a high degree of encapsulation of a therapeutic agent. The nano-emulsion also enables a high degree of internalization to be achieved in the cells linked to a small average diameter of the dispersed phase. Its formulation supports a high concentration of surfactant in the continuous phase and is surprisingly robust, since it remains stable and exhibits a biodistribution of therapeutic agent that does not depend on the composition. Finally, it is of value since it may be formulated so that the surface of the dispersed phase has a low, even zero, zeta potential. Zeta potential is a key parameter which influences the biodistribution of the nano-emulsion. Upon contact with cells, a positive zeta potential thus encourages endocytosis.

In particular, the nano-emulsions advantageously exhibit excellent colloidal stability during storage (>3 months) and a good ability to encapsulate therapeutic agent as well as an increased concentration in the dispersed phase. During application, a long plasma life has also been observed after intravenous injection of the nanoparticles into the organism (stealthy character).

Thus, according to a first aspect, the invention relates to a therapeutic agent formulation in the form of a nano-emulsion, comprising a continuous aqueous phase and at least one dispersed oily phase, in which the oily phase comprises further to the therapeutic agent, at least one amphiphilic lipid and at least one solubilising lipid, and in which the aqueous phase comprises at least one polyalkoxylated cosurfactant.

The amphiphilic lipid is preferably a phospholipid.

The solubilising lipid advantageously comprises at least one fatty acid glyceride, for example a saturated fatty acid glyceride comprising 12 to 18 carbon atoms.

The oily phase may further comprise at least one oil, preferably an oil having a hydrophilic-lipophilic balance (HLB) between 3 and 6, in particular an oil selected from soybean oil and linseed oil.

The cosurfactant preferably comprises at least one chain formed of ethylene oxide units or ethylene oxide and propylene oxide units. The cosurfactant may, in particular, be selected from the conjugated compounds polyethylene glycol/phosphatidylethanolamine (PEG/PE), fatty acid and polyethylene glycol ethers and fatty acid and polyethylene glycol esters, and ethylene oxide and propylene oxide block copolymers.

The therapeutic agent may be, in particular, an active pharmaceutical ingredient or a photosensitizer.

According to a second aspect, the invention relates to a method for preparing a therapeutic agent formulation in the form of a nano-emulsion, comprising at least one continuous aqueous phase and at least one dispersed oily phase, comprising the steps of:

(i) preparing the oily phase comprising at least one solubilising lipid, an amphiphilic lipid and the therapeutic agent;
(ii) preparing an aqueous phase containing a polyalkoxylated cosurfactant;
(iii) dispersing the oily phase in the aqueous phase under the effect of sufficient shear force to form a nano-emulsion; and
(iv) recovering the nano-emulsion thus formed.

The shear force effect is preferably produced by sonication. The oily phase is advantageously prepared by placing all or some of the constituents in solution in an appropriate solvent and subsequently evaporating the solvent.

According to a third aspect, the invention relates to the use of a formulation according to the invention for the administration of a therapeutic agent to humans or animals in order to treat a disease or illness.

The production method according to the invention makes it possible to produce nano-emulsions comprising a very small dispersed phase in a simple, quick and inexpensive manner. The method is also robust and may be carried out easily on an industrial scale. Furthermore, it uses no, or only very few, organic solvents and may be implemented with products approved for human injection. Lastly, only moderate heating is required and so the production method can be used even for labile active ingredients.

DISCLOSURE OF THE INVENTION

Definitions

Within the meaning of this document, the term "nano-emulsion" means a composition having at least two phases, generally an oily phase and an aqueous phase, in which the average size of the dispersed phase is less than 1 micron, preferably 10 to 500 nm and in particular 20 to 100 nm, and most preferably 20 to 70 nm (see article C. Solans, P. Izquierdo, J. Nolla, N. Azemar and M. J. Garcia-Celma, Curr Opin Colloid In, 2005, 10, 102-110).

The term "therapeutic agent" refers to any compound which can be used in the treatment of a disease and which acts in a chemical manner, such as active pharmaceutical ingredients, in a physical or biological manner, but does not include diagnostic agents.

The term "droplet" encompasses droplets of liquid oil as such, as well as the solid particles from oil-in-water emulsions in which the oily phase is solid. In the latter case, the term "solid emulsion" is also often used.

Within the meaning of this document, the term "lipid" denotes all the fats and oils or substances containing fatty acids present in animal fats and in plant oils. They are hydrophobic or amphiphilic molecules mainly formed of carbon, hydrogen and oxygen and having a density lower than that of water. The lipids can be in a solid state at room temperature (25° C.), as in waxes, or liquid as in oils.

The term "phospholipid" refers to lipids having a phosphate group, in particular phosphoglycerides. Most often, phospholipids comprise a hydrophilic end formed by the optionally substituted phosphate group and two hydrophobic ends formed by fatty acid chains. Particular phospholipids include phosphatidylcholine, phosphatidylethanolamine, phosphatidylinositol, phosphatidylserine and sphingomyelin.

The term "lecithin" refers to phosphatidylcholine, i.e. a lipid formed from a choline, a phosphate, a glycerol and two fatty acids. More broadly, it includes phospholipids extracted from living sources, of plant or animal origin, as long as they primarily consist of phosphatidylcholine. These lecithins generally consist of mixtures of lecithins carrying different fatty acids.

The term "fatty acids" refers to aliphatic carboxylic acids having a carbon chain of at least 4 carbon atoms. Natural fatty acids have a carbon chain of 4 to 28 carbon atoms (generally an even number). Long chain fatty acids are those between 14 and 22 carbon atoms long and very long chain fatty acids are those having more than 22 carbon atoms.

The term "surfactant" means compounds having an amphiphilic structure which gives them a specific affinity for oil/water-type and water/oil-type interfaces which enables them to reduce the free energy of these interfaces and to stabilise the dispersed systems.

The term "cosurfactant" means a surfactant acting with another surfactant to further reduce the energy of the interface.

The term "biological ligand" means any molecule which recognises, in a specific manner, a receptor generally arranged at the surface of the cells.

[Emulsion]

According to a first aspect, the invention relates to a therapeutic agent formulation in the form of a nano-emulsion, comprising at least one aqueous phase and at least one oily phase, in which the oily phase also comprises further to the therapeutic agent, at least one amphiphilic lipid and at least one solubilising lipid, and in which the aqueous phase comprises polyalkoxylated cosurfactant.

The emulsion is thus an oil-in-water type emulsion. The emulsion may be single or multiple, in particular by comprising a second aqueous phase in the dispersed phase.

Therapeutic agents capable of being encapsulated in the nano-emulsion according to the invention comprise, in particular, active ingredients acting in a chemical, biological or physical manner. Thus, they may be active pharmaceutical ingredients or biological agents such as DNA, proteins, peptides or antibodies as well as agents useful in physical therapy such as compounds used for thermotherapy, compounds releasing singlet oxygen when excited by light (useful for phototherapy) and radioactive agents. Preferably, they are active ingredients administered via injection.

According to its lipophilic or amphiphilic affinity, the therapeutic agent will be encapsulated by the dispersed phase or situated at the interface between two phases.

The nature of the encapsulated therapeutic agents in the nano-emulsion is not particularly limited. However, the nano-emulsion is of particular value for poorly soluble compounds that are difficult to formulate in conventional administration systems and for luminescent active ingredients useful for phototherapy, of which the quantum yield must be preserved.

On account of the mild conditions for the preparative method, the formulation described is of particular value for encapsulating therapeutic agents that degrade at high temperatures.

Examples of active pharmaceutical ingredients that are of value as therapeutic agents, are in particular, agents used in the treatment of AIDS, agents used in the treatment of heart diseases, analgesics, anaesthetics, anorexigens, anthelmintics, antiallergics, antianginal drugs, antiarrhythmics, anticholinergics, anticoagulants, antidepressants, antidiabetics, antidiuretic, antiemetics, anticonvulsants, antifungal agents, antihistamines, antihypertensives, anti-inflammatories, antimigraine drugs, antimuscarinic drugs, antimycobacterials, anticancer agents, including antiparkinsonians, antithyroid drugs, antivirals, astringents, blocking agents, blood products, blood substitutes, cardiac inotropic agents, cardiovascular agents, agents for the central nervous system, chelators, chemotherapy agents, haematopoietic growth factors, corticosteroids, antitussives, dermatological agents, diurectics, dopaminergics, elastase inhibitors, endocrine agents, ergot alkaloids, expectorants, gastro-intestinal agents, genito-urinary agents, growth hormone factor initiators, growth hormones, haematological agents, haematopoietic agents, haemostatics, hormones, immunological agents, immuninosuppressants, interleukines, interleukine analogues, lipid regulating agents, gonadoliberine, myorelaxants, narcotic antagonists, nutrients, nutrient agents, oncological therapies, organic nitrates, vagomimetics, prostaglandins, antibiotics, renal agents, respiratory agents, sedatives, sexual hormones, stimulants, sympathomimetics, systemic anti-infectives, tacrolimus, thrombolytic agents, thyroid agents, treatments for attention difficulties, vaccines, vasodilators, xanthines and cholesterol-reducing agents. Those particularly concerned are anticancer agents such as taxol (paclitaxel), doxorubicin and cisplatin.

Examples of physical agents are, in particular, radioactive isotopes and photosensitizers.

Examples of photosensitizers are, in particular, those belonging to the class of tetrapyrroles, such as porphyrins, bacteriochlorines, phthalocyanins, chlorines, purpurines, porphycenes, pheophorbides, or those belonging to the class of texaphyrins or hypericins. Examples of first generation photosensitizers are haemato-porphyrin and a mixture of haemato-porphyrin derivatives (HpD) (sold under the trade name Photofrin® by Axcan Pharma). Examples of second generation photosensitizers are meta-tetra-hydroxyphenyl chlorine (mTHPC; trade name Foscan®, Biolitec AG) and the monoacid derivative of the A ring of benzoporphyrin (BPD-MA sold under the trade name Visudyne® by QLT and Novartis Opthalmics). Formulations of second generation photosensitizers that associate, with these photosensitizers, a molecule (lipid, peptide, sugar etc.) which acts as a transporter and permits their selective routing in tumour tissue are called third generation photosensitizers.

Examples of biological agents are oligonucleotides, DNA, RNA, siRNA, peptides and proteins.

The therapeutic agent may of course be formulated directly in its active form or in the form of a prodrug. In addition, it is possible for a plurality of therapeutic agents to be formulated in association in the nano-emulsion.

The amount of therapeutic agent depends on the intended application concerned as well as on the nature of the agent. However, an attempt is generally made to formulate the nano-emulsion with a maximum concentration of therapeutic agent, in particular when using poorly soluble therapeutic agents, so as to limit the volume and/or the duration of administration to the patient.

Now, it has been found the presence of the solubilising lipid in the oily phase makes it possible to incorporate a large quantity of compounds, even hydrophobic or amphiphilic compounds.

The formulation according to the invention will more often contain a quantity of 0.001 to 30% by weight, preferably 0.01 to 20% by weight, or even more preferably 0.1 to 10% by weight of therapeutic agent.

Advantageously, the therapeutic agents are incorporated in the emulsion in solution form, and the solvent is then separated, for example by evaporation. The solution contains the therapeutic agent in a variable quantity that may reach its solubility limit. The choice of solvent depends on the solubility of each therapeutic agent. The solvents employed may be, for example, methanol, ethanol, chloroform, dichloromethane, hexane, cyclohexane, DMSO, DMF or even toluene. A volatile solvent, preferably non-toxic to humans, is preferably used.

According to the invention, the oily phase of the nano-emulsion further comprises at least one amphiphilic lipid and at least one solubilising lipid.

So as to form a stable nano-emulsion, it is generally necessary to include in the composition at least one amphiphilic lipid as a surfactant. The amphiphilic nature of the surfactant makes the oil droplets stable within the aqueous continuous phase.

The amphiphilic lipids comprise a hydrophilic part and a lipophilic part. They are generally selected from compounds of which the lipophilic part comprises a linear or branched saturated or unsaturated chain having 8 to 30 carbon atoms. They may be selected from phospholipids, cholesterols, lysolipids, sphingomyelins, tocopherols, glucolipids, stearylamines and cardiolipins, and may be of natural or synthetic origin; molecules formed of a fatty acid coupled to a hydrophilic group by an ether or ester function, such as sorbitan esters, for example sorbitan monooleate and sorbitan monolaurate sold under the Span® trade names by Sigma; polymerised lipids; lipids conjugated to short chains of polyethylene oxide (PEG), such as the non-ionic surfactants sold under the trade names Tween® by ICI Americas, Inc. and Triton® by Union Carbide Corp.; sugar esters such as sucrose monolaurate and sucrose dilaurate, sucrose monopalmitate and sucrose dipalmitate, sucrose monostearate and sucrose distearate; it being possible to use said surfactants alone or in a mixture.

Lecithin is the preferred amphiphilic lipid.

In one specific embodiment, all or part of the amphiphilic lipid may have a reactive function, such as a maleimide, thiol, amine, ester, oxyamine or aldehyde group. The presence of reactive functions allows functional compounds to graft at the interface. The reactive amphiphilic lipid is incorporated into the layer formed at the interface stabilising the dispersed phase, where it is liable to couple to a reactive compound present in the aqueous phase for example.

Generally, the oily phase will comprise 0.01 to 99% by weight, preferably 5 to 75% by weight, in particular 20 to 60% by weight and most particularly 33 to 45% by weight amphiphilic lipid.

The amount of amphiphilic lipid advantageously helps to control the size of the dispersed phase of the nano-emulsion obtained.

The emulsion according to the invention further comprises a solubilising lipid. The main task of this compound is to solubilise the amphiphilic lipid, which is poorly soluble, in the oily phase of the nano-emulsion.

The solubilising lipid is a lipid having a sufficient affinity for the amphiphilic lipid to allow it to be solubilised. The solubilising lipid is preferably solid at room temperature.

In the case where the amphiphilic lipid is a phospholipid, possible solubilising lipids are, in particular, glycerol derivatives, especially glycerides obtained by esterifying glycerol with fatty acids.

The solubilising lipid used is advantageously selected in dependence on the amphiphilic lipid used. It will generally have a close chemical structure so as to bring about the desired solubilisation. It may be an oil or a wax. The solubilising lipid is preferably solid at room temperature (20° C.), but liquid at body temperature (37° C.).

The preferred solubilising lipids, in particular for phospholipids, are fatty acid glycerides, in particular saturated fatty acid glycerides, and in particular saturated fatty acid glycerides comprising 8 to 18 carbon atoms, even more preferably 12 to 18 carbon atoms. Advantageously, a mixture of different glycerides is involved.

Preferably, saturated fatty acid glycerides comprising at least 10% by weight C12 fatty acids, at least 5% by weight C14 fatty acids, at least 5% by weight C16 fatty acids and at least 5% by weight C18 fatty acids are involved.

Preferably, saturated fatty acid glycerides comprising 0% to 20% by weight C8 fatty acids, 0% to 20% by weight C10 fatty acids, 10% to 70% by weight C12 fatty acids, 5% to 30% by weight C14 fatty acids, 5% to 30% by weight C16 fatty acids and 5% to 30% by weight C18 fatty acids are involved.

The semi-synthetic glyceride mixtures sold by Gattefossé under the trade name Suppocire® NC, which are solid at room temperature and have been approved for human injection, are particularly preferred. The type N Suppocire® glycerides are obtained by direct esterification of fatty acids and glycerol. These are semi-synthetic glycerides of C8 to C18 saturated fatty acids, of which the quali-quantitative composition is shown in the table below.

The aforementioned solubilising lipids make it possible to obtain a formulation in the form of a nano-emulsion which is advantageously stable. Without wanting to draw on a specific theory, it is assumed that the aforementioned solubilising lipids make it possible to obtain droplets in the nano-emulsion having an amorphous core. The core thus obtained has an increased inner viscosity without exhibiting crystallinity. Crystallisation has an adverse effect on the stability of the nano-emulsion since it generally causes the droplets to aggregate and/or causes the encapsulated molecules to be expelled from the droplets. These properties thus promote the physical stability of the nano-emulsion and the stability of the encapsulation of the therapeutic agent over time.

The amount of solubilising lipid may vary widely as a function of the type and amount of amphiphilic lipid present in the oily phase. Generally, the oily phase will comprise 1 to 99% by weight, preferably 5 to 80% by weight and in particular 40 to 75% by weight solubilising lipid.

TABLE 1

| Fatty acid composition of Suppocire NC ® from Gattefossé | |
|---|---|
| Chain length | [% by weight] |
| C8 | 0.1 to 0.9 |
| C10 | 0.1 to 0.9 |
| C12 | 25 to 50 |
| C14 | 10 to 24.9 |
| C16 | 10 to 24.9 |
| C18 | 10 to 24.9 |

The oily phase may further comprise one or more other oils.

The oils used preferably have a hydrophilic-lipophilic balance (HLB) of less than 8 and even more preferably of between 3 and 6. Advantageously, the oils are used without any chemical or physical modification in advance of the formation of the emulsion.

In the proposed applications, the oils may be selected from biocompatible oils, in particular from oils of natural (plant or animal) or synthetic origin. Oils of this type include, in particular, oils of natural plant origin, including in particular soybean, linseed, palm, peanut, olive, grape seed and sunflower oils; and synthetic oils, including in particular triglycerides, diglycerides and monoglycerides. These oils may be in their natural form, refined or interesterified.

The preferred oils are soybean oil and linseed oil.

Generally, if present, the oil is contained in the oily phase in an amount ranging from 1 to 80% by weight, preferably between 5 and 50% by weight and in particular from 10 to 30% by weight.

The oily phase may further contain other additives, such as colourings, stabilisers, preservatives, fluorophores, contrast agents for imaging, inorganic nanocrystals (for example gold, iron oxide or semiconductor nanocrystals) or other active ingredients in an appropriate amount.

The oily phase for the dispersed phase of the emulsion may be prepared by simply mixing the constituents, heating them if necessary until all the constituents have melted.

The aqueous phase used in the method according to the invention preferably consists of water and/or a buffer, such as a phosphate buffer, for example PBS ("phosphate buffered saline") or another saline solution, in particular sodium chloride.

Moreover, it optionally comprises other ingredients, including a cosurfactant. The cosurfactant stabilises the nano-emulsion.

The cosurfactant may also have other effects in the intended application of the nano-emulsion. In particular, it may be grafted so as to carry a targeting ligand.

The cosurfactants which may be used in emulsions according to the present invention are preferably water-soluble surfactants. The water-soluble surfactants are preferably alkoxylated and preferably comprise at least one chain composed of ethylene oxide units (PEO or PEG) or ethylene oxide and propylene oxide units. Preferably, the number of units in the chain varies between 2 and 500.

Examples of cosurfactants include, in particular, the conjugated compounds polyethylene glycol/phosphatidylethanolamine (PEG-PE), fatty acid and polyethylene glycol ethers such as the products sold under the Brij® trade names (for example Brij® 35, 58, 78 or 98) by ICI Americas Inc., fatty acid and polyethylene glycol esters such as the products sold under the Myrj® trade names by ICI Americas Inc. (for example Myrj® 45, 52, 53 or 59) and ethylene oxide and propylene oxide block copolymers such as the products sold under the Pluronic® trade names by BASF AG (for example Pluronic® F68, F127, L64, L61, 10R4, 17R2, 17R4, 25R2 or 25R4) or the products sold under the Synperonic® trade name by Unichema Chemie BV (for example Synperonic® PE/F68, PE/L61 or PE/L64).

The aqueous phase comprises 0.01 to 50% by weight, preferably 1 to 30% by weight, and in particular 5 to 20% by weight of a cosurfactant.

In a preferred embodiment, the continuous phase further comprises a thickening agent such as a glycerol, a saccharide, oligosaccharide or polysaccharide, a gum or even a protein; preferably glycerol. In fact, the use of a continuous phase of a higher viscosity facilitates emulsification and thus allows the sonication time to be reduced.

The aqueous phase advantageously comprises 0 to 50% by weight, preferably 1 to 30% by weight and in particular 5 to 20% by weight of a thickening agent.

Naturally, the aqueous phase may further comprise other additives such as colourings, stabilisers and preservatives in appropriate amounts.

The aqueous phase for the continuous phase of the emulsion may be prepared by simply mixing the different constituents with the selected aqueous medium.

[Preparation Method]

The nano-emulsion described above may be prepared easily by dispersing suitable amounts of oily phase and aqueous phase under the effect of a shear force.

In the method according to the invention, the different oily constituents and the therapeutic agent are initially mixed to prepare an oily premix for the dispersed phase of the emulsion. The mixing may optionally be facilitated by placing one of the constituents or the complete mixture in solution in an appropriate organic solvent. The organic solvent is then evaporated so as to obtain a homogeneous oily premix for the dispersed phase.

Furthermore, it is preferred to produce the premix at a temperature at which all of the ingredients are liquid.

According to a preferred embodiment, the dispersed phase of the nano-emulsion is grafted at the surface with beneficial molecules, such as biological ligands. A grafting process of this type makes it possible to recognise specific cells (for example tumour cells as described, for example, in the article by S. Achilefu, Technology in Cancer Research & Treatment, 2004, 3, 393-408) or specific body organs.

The surface grafting process is preferably achieved by coupling molecules or their precursors with an amphiphilic compound, in particular with the cosurfactant. In this case, the amphiphilic compound acts as a spacer enabling the targeting molecules to be arranged at the surface. This coupling may be carried out before or after emulsification. The latter case may be preferred when the chemical reactions used are compatible with the colloidal stability of the emulsions, in particular with regard to pH. The pH during the coupling reaction is preferably between 5 and 11.

The beneficial molecules may be, for example:

biological targeting ligands, such as antibodies, peptides, saccharides, aptamers, oligonucleotides or compounds, such as folic acid;

a stealth agent: a substance added so as to make the nano-emulsion invisible to the immune system, to increase its circulation time within the organism and to slow down its elimination.

It is also possible to introduce inside the nanoparticles, at the surface thereof or adsorbed thereon, by way of a covalent bond or not:

imaging agents, in particular for MRI (magnetic resonance imaging), PET (positron emission tomography), SPECT (single photon emission computed tomography), ultrasonography, radiography, X-tomography and optical imaging (fluorescence, bioluminescence, diffusion, etc.); and/or therapeutic agents as defined above.

The proportion of oily phase and aqueous phase is highly variable. However, usually, the nano-emulsions will be prepared with 1 to 50%, preferably 5 to 40%, and in particular 10 to 30% by weight oily phase and 50 to 99%, preferably 60 to 95% and in particular 70 to 90% by weight aqueous phase.

Advantageously, the oily phase is dispersed in the aqueous phase in a liquid state. If one of the phases solidifies at room temperature, it is preferable to make the mixture with one, or preferably the two phases heated to a temperature greater than or equal to the melting temperature.

The emulsification under shear force effect is preferably produced using a sonicator or a microfluidiser. Preferably, the aqueous phase and then the oily phase are introduced into an appropriate cylindrical receptacle in the desired proportions and the sonicator is dipped into the medium and switched on for long enough to obtain a nano-emulsion, usually a few minutes.

This produces a homogeneous nano-emulsion in which the average diameter of the oil droplets is greater than 10 nm and less than 200 nm, preferably between 20 and 50 nm.

The absolute value of the zeta potential is preferably lower than 20 mV, that is to say between −20 and 20 mV.

Before conditioning, the emulsion may be diluted and/or sterilised, for example by filtration or by dialysis. This step makes it possible to eliminate any aggregates which might have formed during preparation of the emulsion.

The emulsion thus obtained is ready to use, after dilution if necessary.

[Methods of Use]

The formulation according to the invention may be used as it stands or adapted to the intended application, for example by way of dilution, for administration of the therapeutic agent(s) to humans or animals.

Owing to the fact that it may be prepared exclusively from constituents approved for humans, the formulation is particularly suitable for parenteral administration. However, it is also possible for administration to be achieved by other routes, in particular orally or topically.

The formulation disclosed thus enables a simple method for administering therapeutic agents which are necessary for treating illnesses, such as cancer, by way of chemotherapy or phototherapy in particular.

The present invention also relates to a therapeutic treatment method comprising administration of an effective therapeutic amount of the formulation as defined above to a mammal, preferably a human, in need thereof.

Figure 2:
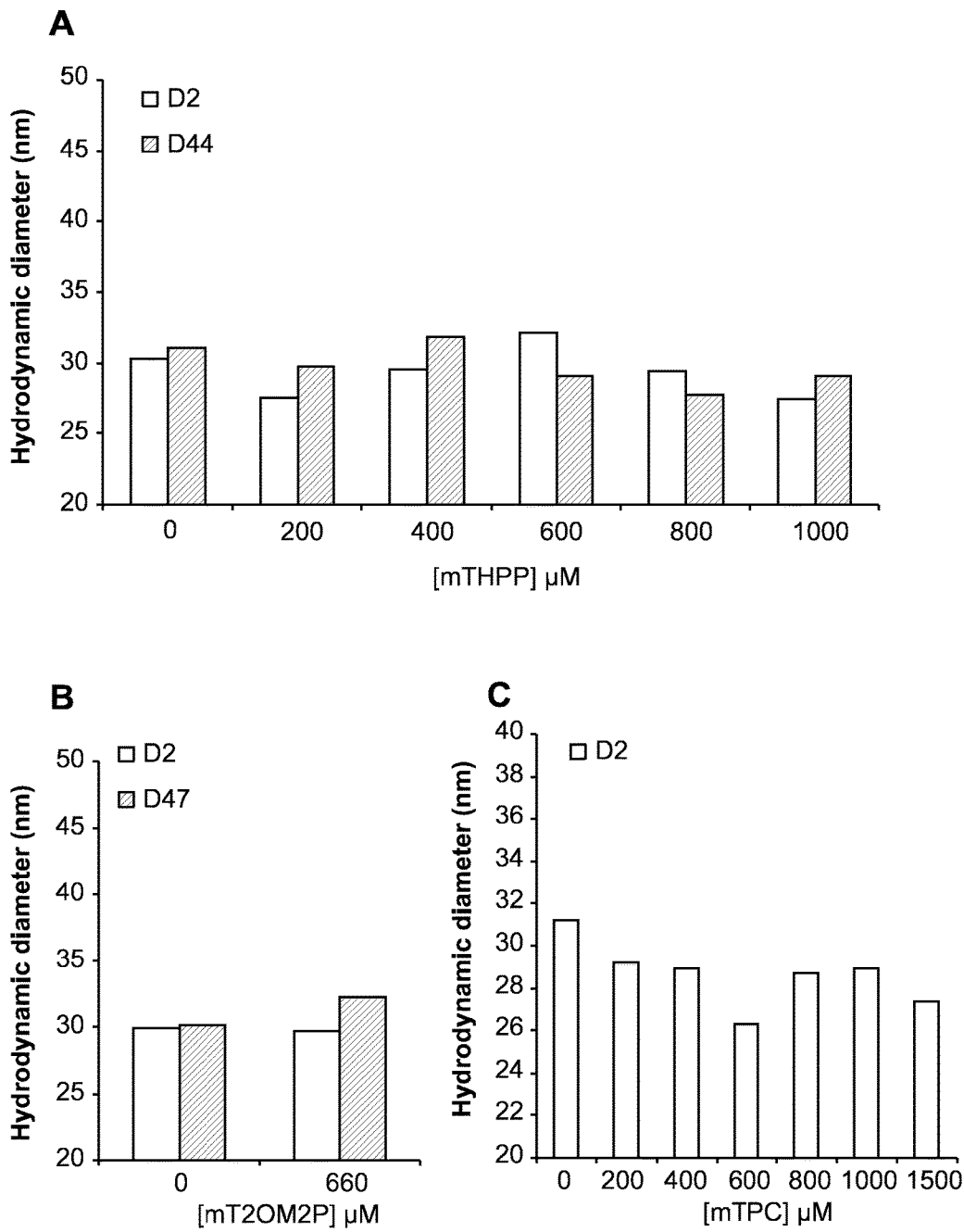
Figure 3:
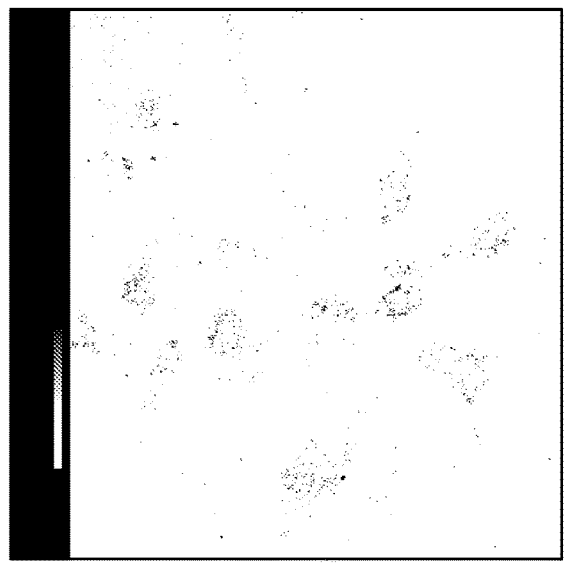
Figure 4:
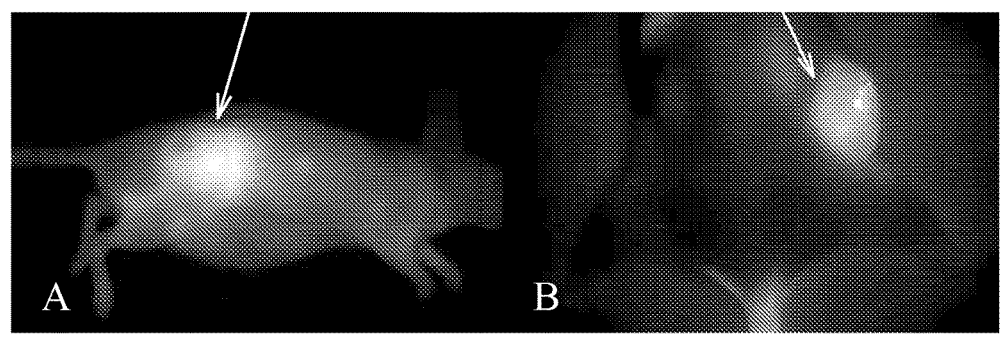
Figure 5:
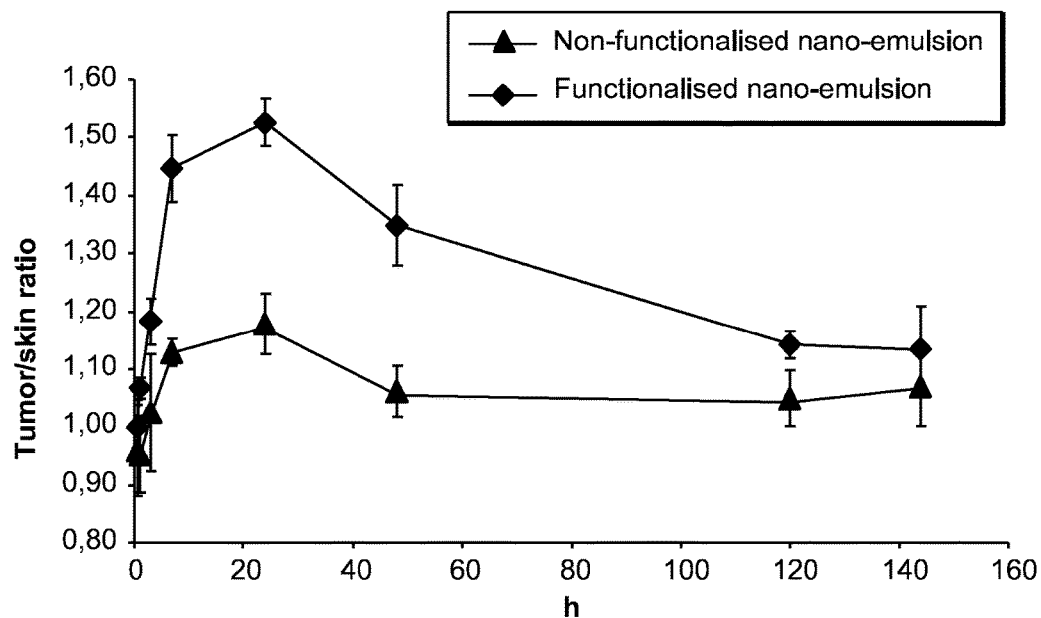
Figure 6:
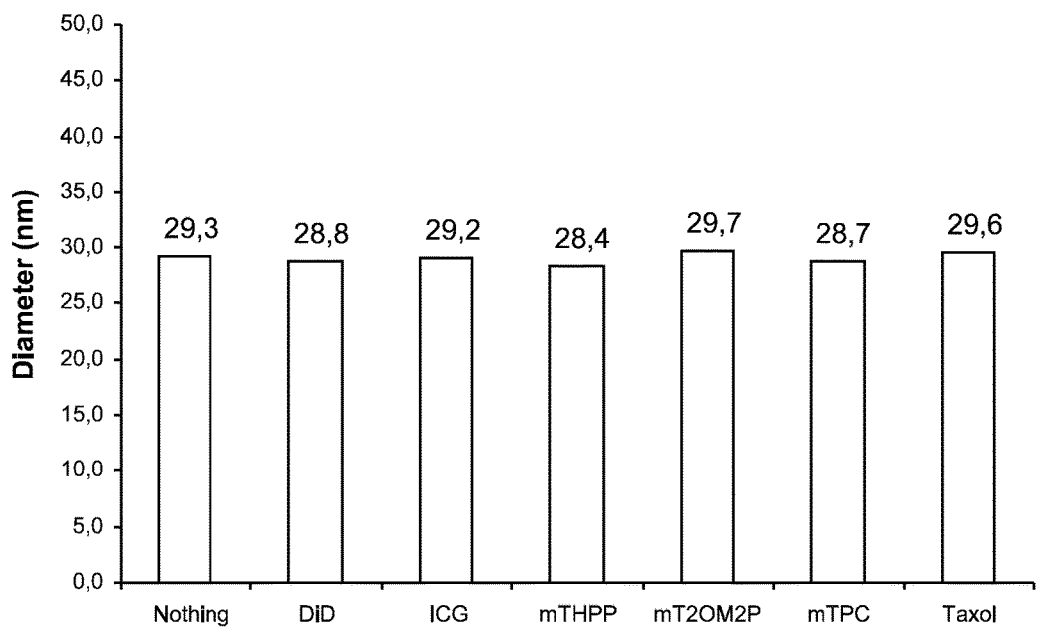

The invention will be described in greater detail hereinafter by way of the Examples below and accompanying figures, in which:

FIG. 1: shows the optical density at 650 nm of nano-emulsions of mTHPP and mTPC according to Examples 2A and 2C with a respective loading rate of 0 to 1000 µM of mTHPP and from 0 to 2000 µM of mTPC, before and after dialysis, determined by a CARY 300-SCAN spectrophotometer and represented respectively in A and B. The equation of the linear correlation straight lines before dialysis are, for mTHPP: y=0.0042x+0.2331 (R=0.99) and, for mTPC: y=0.0049x+0.023 (R=0.99), those of the straight lines after dialysis are, for mTHPP: y=0.0056x+0.1503 (R=0.99) and, for mTPC: y=0.0059x+0.0584 (R=0.99);

FIG. 2: shows bar charts of the average diameter of the dispersed phase of the emulsions according to Examples 2A-2C measured after dialysis on the Zetasizer (Malvern Instruments) (samples diluted at 1:1000 in PBS 0.1×);

FIG. 3: shows images of cells obtained in Example 3 observed in confocal microscopy in the near infrared. Black grains represent the fluorescence emitted by mTHPP;

FIG. 4: shows mice carrying a sub-cutaneous tumour of the Ts/Apc type (10 million cells). Observation 24 h after iv injection on anaesthetised mice of 200 µL of nano-emulsion solution with 50 µM fluorophore (A: nano-emulsions encapsulating DiD; B: nano-emulsions encapsulating ICG);

FIG. 5: shows the development of the ratio of the fluorescence signal emitted by the tumour to the fluorescence signal emitted by the skin as a function of time for nano-emulsions functionalised by cRGDs and non-functionalised nano-emulsions, and FIG. 6: shows the average diameter of the dispersed phase of various nano-emulsions as a function of the molecule incorporated in the lipophilic core.

Figure 7:
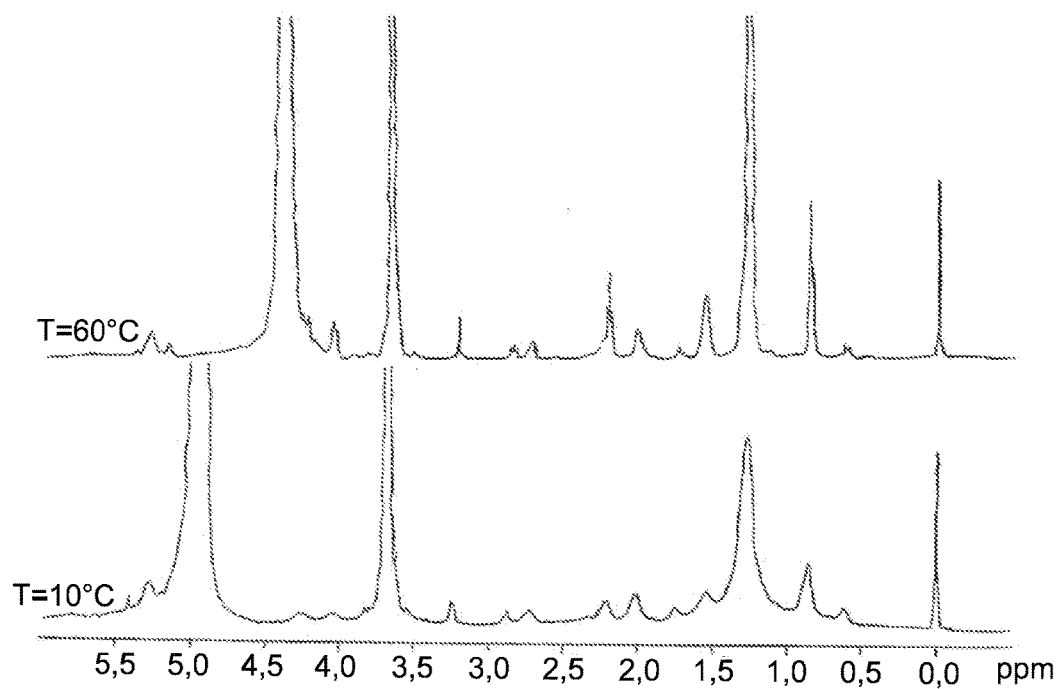

FIG. 7: shows two $^1$H NMR spectra of the nano-emulsions after production for temperatures T=10° C. and T=60° C. (Example 6).

Figure 8:
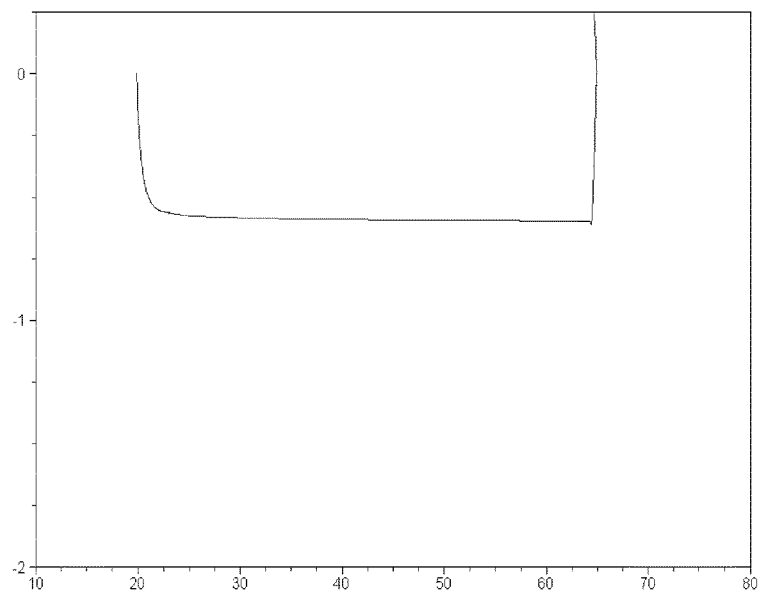
Figure 8:
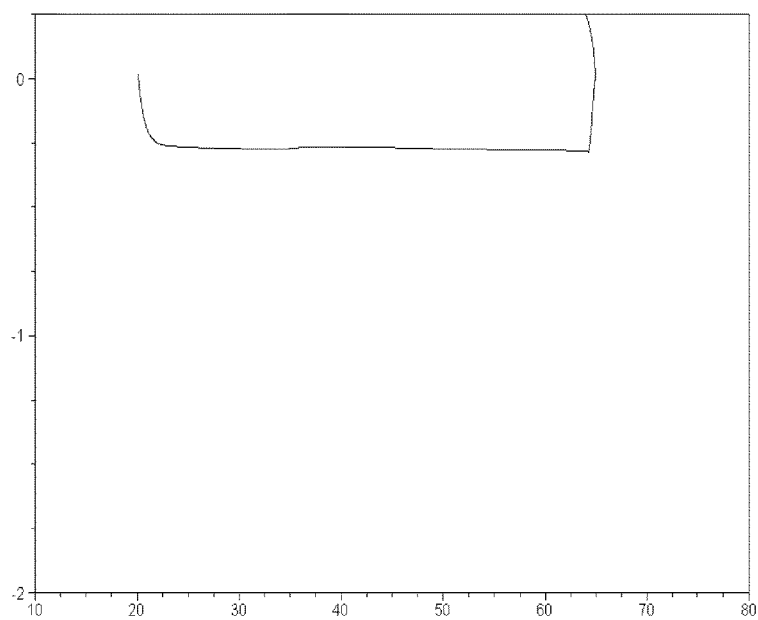

FIG. 8: shows thermograms (heat flow (W/g) as a function of temperature in ° C.) obtained by differential scanning calorimetry (DSC) of the nano-emulsions after production (a) and after 4 months of storage at room temperature (b) using a Universal V3.8B TA instrument (Example 6).

Figure 9:
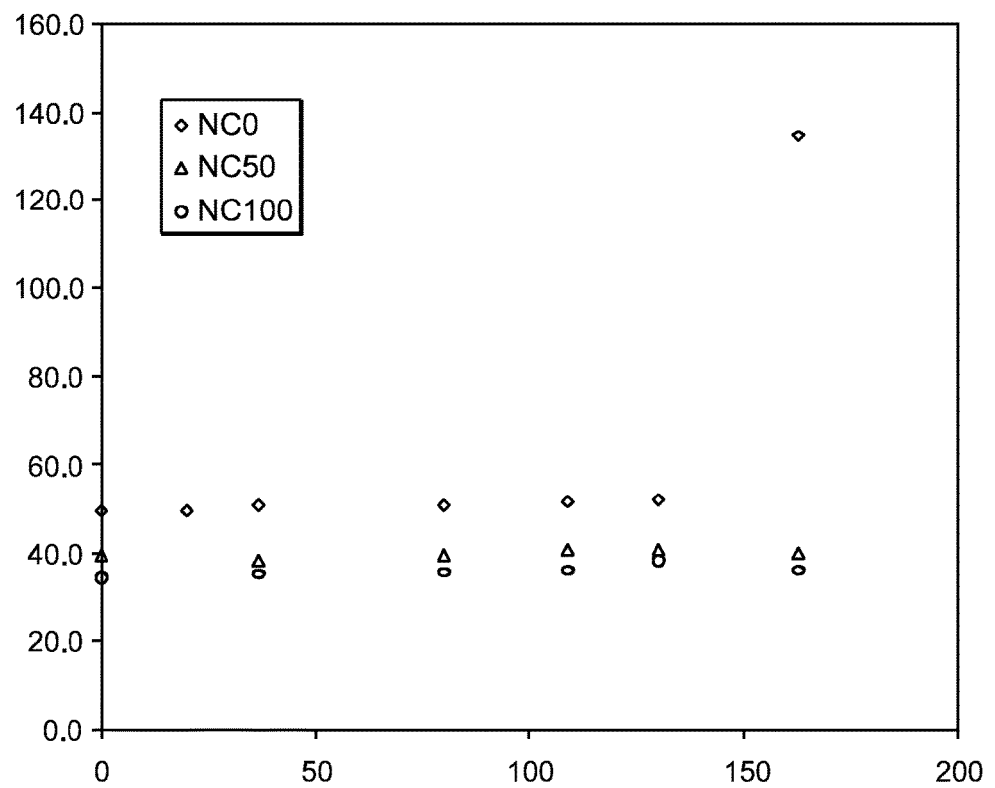

FIG. 9: shows the development of the size of the droplets (in nm) of the nano-emulsion as a function of time (in days) for three nano-emulsions at 40° C. The diamonds represent a nano-emulsion containing no solubilising lipid and comprising oil, the triangles represent a nano-emulsion comprising a 50:50 mixture of solubilising lipid and oil and the circles represent a nano-emulsion containing no oil and containing solubilising lipid (Example 6).

EXAMPLES

Example 1

Preparation of a Nano-Emulsion Encapsulating Paclitaxel

A batch of 2 mL of nano-emulsion encapsulating paclitaxel (initial paclitaxel load of 1 mM, i.e. 850 µg/mL) was prepared in the following manner.

The oily phase was prepared by introducing, 190 mg of semi-synthetic glycerides sold under the trade name Suppocire® NC (Gattefossé) and 138 mg of soy lecithin (L-α-phosphatidylcholine, sold by Fluka), ≥30% phosphatidylcholine) into a suitable receptacle heated to 50° C. 17 mg of paclitaxel (sold by Sigma-Aldrich) dissolved in 1 mL of chloroform (i.e. 0.002 mmol of paclitaxel) were added to this mixture and the mixture was then homogenised by vortex mixing. The solvent was then evaporated under vacuum at 40-45° C. in a rotary evaporator while progressively reducing the pressure.

The aqueous phase was prepared by introducing 228 mg of Myrj 53 (polyethoxylated surfactant sold by Sigma-Aldrich) into a 2 mL Vial and then adding 1.38 mL (1444 mg) of a saline solution ([NaCl]=154 mM). The mixture was heated to 50° C. so as to melt the surfactant and the solution obtained was then homogenised by vortex mixing. The aqueous solution was held at 50° C.

The oily phase and then the aqueous phase (at 50° C.) were then introduced into a flask immersed in a water bath at 50° C. The biphasic solution was then put into contact with a sonicator fitted with a conical probe (Vibra-cell 75115 sold by Bioblock Scientific) dipping approximately 1 cm in the mixture. The mixture was sonicated lightly for 5 minutes with the sonicator adjusted to 25% of the maximum power, with the following sequence of pulses: 10 seconds of sonication/30 seconds rest.

The nano-emulsion obtained was then filtered through a 0.2 mM filter so as to separate any non-encapsulated taxol. The concentration of lipid nanoparticles in the nano-emulsion obtained was approximately 25% by weight.

The nano-emulsion was then ready for pharmaceutical use and was concentrated to an amount determined as 612 µg/mL of paclitaxel (i.e. 50 mL of a solution to be injected for a therapeutic dose of 30 mg) in a saline buffer ready for therapeutic injection (154 mM NaCl). The formulation is summarized in table 2 below.

TABLE 2

| Composition of the formulation of Example 1 | | |
|---|---|---|
| | Constituents | Weight mg |
| Dispersed phase | Suppocire NC | 190 |
| Continuous phase | Saline solution | 1444 |
| Surfactants | Lecithin | 138 |

TABLE 2-continued

Composition of the formulation of Example 1

| | Constituents | Weight mg |
|---|---|---|
| | Myrj 53 | 228 |
| Dopant | Paclitaxel | 1.7 |

Analysis of Encapsulated Taxol

The paclitaxel encapsulated in the nano-emulsion obtained was analyzed by HPLC according to the method developed from the study by S. Kim et al., (S. C. Kim, J. Yu, J. W. Lee, E.-S. Park, S.-C. Chi, *Journal of Pharmaceutical and Biomedical analysis*, 2005, 39 170-176).

First of all, the satisfactory physico-chemical behaviour of taxol under the conditions for preparing the nano-emulsion and for analysis was confirmed, by verifying the absence of degradation after submission to ultrasound, heat treatment (4 h at 60° C.) and under the analytical conditions (in an acetonitrile/water mixture).

The HPLC (high performance liquid chromatography) apparatus used was as follows:
  Detection module: Dual A Absorbance Detector Waters 2487, UV detection at 227 nm
  Separation module: Separations module Waters 269
    Column: Supelco phase Supelcosil C18 250×4.6 mm, 5 µm, flow rate 1 mL/min.
    Volume injected: 20 µL of solution (1 mg/mL of taxol in methanol, i.e. 1.17 mM).
    Mobile phase: $CH_3CN/H_2O$.
    The retention time of taxol was $t_R$=14.64 min for an elution gradient indicated in table 3 below:

TABLE 3

Elution gradient used

| Time (min) | % $H_2O$ | % ACN |
|---|---|---|
| 0 | 66 | 34 |
| 2 | 66 | 34 |
| 15 | 30 | 70 |
| 19 | 66 | 34 |
| 44 | 66 | 34 |

For quantitative analysis, an internal standard was used, ethyl 4-dimethylaminobenzoate (EI) ($C_{11}H_{15}NO_2$, sold by Sigma-Aldrich) which had a retention time of $t_R$ (EI)=15.256 min under the conditions detailed above. The encapsulated taxol was extracted from the nano-emulsion by breaking the emulsion, extracting taxol from the mixture and adding a known quantity of internal standard for analysis by HPLC. The result obtained was compared with a previously prepared calibration curve representing the ratio between the areas A of the peaks between taxol and the internal standard.

A taxol concentration of 0.597 mM was found (theoretical concentration 0.83 mM), and hence a degree of encapsulation of at least 72%.

Example 2A

Preparation of a Nano-Emulsion Encapsulating a Photosensitizer (mTHPP)

A nano-emulsion encapsulating 5,10,15,20-tetrakis(4 hydroxyphenyl)-(21H,23H)-porphyrin (mTHPP) sold by Sigma-Aldrich was prepared as follows.

0.05 g of soybean oil (Sigma-Aldrich) was introduced into a suitable receptacle together with 0.150 g of semi-synthetic glycerides (sold under the trade name Suppocire® NC (Gattefossé)), and 0.100 g of soy lecithin (enriched to 75% phosphatidylcholine, sold by Lipoïd under the trade name Lipoïd® 75). A quantity of between 0.27 mg and 1.37 mg of 5,10,15,20-tetrakis(4 hydroxyphenyl)-21H,23H-porphyrin, (mTHPP sold by Sigma-Aldrich) was added to this premix in solution in dimethyl sulfoxide (DMSO). After evaporating off the solvent under vacuum, the residue was heated to 50-60° C. and the liquid mixture was kept at this temperature for emulsification.

In another receptacle, a mixture was prepared of 0.05 g of glycerol, 0.331 g of polyoxyethylene stearate having 50 moles of ethylene oxide (sold under the trade name Myrj® 53 by ICI Americas Inc.) and sodium chloride in 154 mM aqueous solution to give 1.7 g. The aqueous solution obtained was kept hot (50-60° C.).

The oily phase and then the aqueous phase, heated to 50° C., were introduced into a flask immersed in a water bath at 50° C. The biphasic solution was then put into contact with an AV505® sonicator fitted with a conical probe measuring 3 mm in diameter (Sonics, Newtown) dipping approximately 1 cm into the solution. The solution was then sonicated for 5 minutes with the sonicator adjusted to 25% of the maximum power with the following sequence of pulses: 10 seconds of sonication/30 seconds rest. During sonication, the solution was kept at 50° C. in a water bath.

The emulsion obtained was dialysed against a 154 mM sodium chloride solution with a Spectra/Por® dialysis membrane having a cut-off threshold equal to 12000 so as to remove reactants that had not reacted. The emulsion obtained was then filtered through a 0.22 µm filter so as to sterilize it and to remove any aggregates and excess photosensitizer.

This emulsion could be kept as it was and then be used directly after possible dilution for therapeutic application without previous special treatment such as resuspension.

Table 4 below summarises the composition of the formulation obtained before dialysis. The mean degree of incorporation of mTHPP in the nano-emulsion, calculated from the optical density, was approximately 75% (FIG. 1).

TABLE 4

Composition of the formulation of examples 2A-2C

| | Constituents | Weight mg | % by weight |
|---|---|---|---|
| Dispersed phase | Soybean oil | 50 | 2.5 |
| | Suppocire ®NC | 150 | 7.5 |
| Photosensitizers | | 0.24-2.4 | 0.012-0.12 |
| Surfactants | Lecithin | 100 | 5 |
| | Myrj 53 | 331 | 16.55 |
| | Glycerol | 50 | 2.5 |
| Aqueous phase | 154 mM NaCl Solution | 1319 | 65.95 |
| Total | | 2000 | 100 |

The emulsions obtained in this way had an average diameter of the dispersed phase determined by light diffusion (ZeiterSizer Nano, Malvern Instrument) of 29 nm, as illustrated in FIG. 2.

Moreover, this formulation of photosensitizers was very stable for at least 40 days as demonstrated by the stability of the average diameter of the dispersed phase over time illustrated in FIGS. 2A and 2B.

With regard to all these properties, the formulation according to the invention could therefore be marketed in a ready-to-use form.

Example 2B

Preparation of a Nano-Emulsion Encapsulating a Photosensitizer (mT2OM2P)

Example 2A was repeated in an identical manner except that the photosensitizer was replaced by a quantity of 2.3 mg of 5,10,15,20-tetrakis(4 octadecyloxymethylphenyl)-21H, 23H-porphyrin (mT2OM2P, sold by Porphyrin systems) directly in the premix.

Table 4 above summarises the composition of the formulation obtained before dialysis. The mean degree of incorporation of mT2OM2P in the nano-emulsion obtained, calculated from the optical density, was approximately 89%.

Example 2C

Preparation of a Nano-Emulsion Encapsulating a Photosensitizer (mTPC)

Example 2A was repeated in an identical manner except that the photosensitizer was replaced by a quantity of between 0.24 mg and 2.4 mg of meso-tetraphenylchlorine (mTPC, sold by Porphyrin Systems) added in the form of a 10 mM solution in toluene.

Table 4 above summarises the composition of the formulation obtained before dialysis. The mean degree of incorporation of mTPC in the nano-emulsion obtained, calculated from the optical density, was approximately 83% FIG. 1.

Measurement of the Fluorescence Quantum Yield

The fluorescence quantum yield of various photosensitizers formulated in a nano-emulsion and in solvent was measured with reference to Nile Blue perchlorate in ethanol, $\lambda_{exc}$ 605 nm ($F_{ref}$=0.27). The results are summarised in table 5. It was found that the yields were substantially those of the photosensitizers in their respective solvents. The formulation in a nano-emulsion did not therefore affect the fluorescence quantum yield of the photosensitizers tested.

TABLE 5

| Fluorescence quantum yield F | |
| --- | --- |
| Photo-sensitizers | F |
| mTHPP in ethanol | 0.23 |
| mTHPP (nano-emulsion, loading rate 800 μM) | 0.23 |
| mT2OM2P (nano-emulsion, loading rate 660 μM) | 0.16 |
| mTPC in toluene | 0.38 |
| mTPC (nano-emulsion, loading rate 800 μM) | 0.40 |

Example 3

Internalisation of Nano-Emulsions in Tumour Cells

The internalisation of nano-emulsions encapsulating mTHPP (loading rate 600 μM) obtained according to Example 2A in tumour cells of the U373 line was monitored in vitro by fluorescence microscopy.

The U373 tumour cells, placed in culture chambers on slides (Labtech, Nunc) were incubated for 24 h in a controlled atmosphere containing 5% $CO_2$ in the presence of mTHPP formulated in a nano-emulsion according to Example 2 at a final concentration of 2 μM in the DMEM culture medium (provided by Gibco, Invitrogen). After a series of rinsing operations using DMEM and fixing at 37° C. in a 4% paraformaldehyde solution, the cells were placed in a special mounting medium for fluorescence (Prolong anti-fade, Invitrogen) and the slides were covered with cover slips.

Confocal microscopy (Leica TS2) of the samples showed fluorescence in tumour cells, as illustrated in FIG. 3, demonstrating the passage of mTHPP formulated in a nano-emulsion from outside the tumour cell to the interior.

Example 4

Passive Accumulation in Various Tumour Models

The biodistribution of nano-emulsions according to the invention was studied in mice carrying tumours and using non-invasive fluorescence imaging.

For these requirements, nano-emulsions were prepared according to Examples 1 and 2 except that, instead of the encapsulated therapeutic agent, a lipophilic or amphiphilic organic fluorophore adapted for non-invasive fluorescence imaging in vivo (fluorophore DiD or DiR, Invitrogen, and ICG Sigma) was used, as described in patent application PCT FR2007/000269.

The cells acting as a tumour model were Ts/Apc cells that came from a murine breast cancer (Ts/Apc) (Lollini, P. L.; Degiovanni, C.; Landuzzi, L.; Nicoletti, G.; Frabetti, F.; Cavallo F.; Giovarelli, M.; Formi, G.; Modica, A.; Modesti, A.; Musiani, P.; Nanni, P.; Human Gene Therapy 1995, 6, (6), 743-752). The Ts/Apc cells were cultivated in an RPMI 1640 culture medium comprising 10% FCS, 50 U/mL of penicillin, 50 μg/mL of streptomycin, 2-mercaptoethanol at $2.5 \times 10^{-5}$ M (sold by Sigma-Aldrich). The cells were kept at 37° C. in a moist atmosphere with 5% $CO_2$. $10^6$ cells were injected subcutaneously in the back of female nude mice 5-6 weeks old (IFFA-Credo, Marcy l'Etoile, France) 2 weeks before the nano-emulsions were injected. All injections and acquisitions of images were performed while the mice were kept under general anaesthesia by way of gas (isoflurane). The anaesthetised animals were imaged with fluorescence reflectance imaging (FRI) devices adapted to the spectral properties of encapsulated fluorophores.

FIG. 4 shows the fluorescence signal obtained 24 h after injection. The image clearly shows the accumulation of the fluorescent tracer in the tumour, for the two different fluorophores.

Example 5

Preparation of Functionalised Nano-Emulsions

Nano-emulsions could be functionalised using functionalizable surfactants so as to increase their accumulation in the tumour by an active targeting phenomenon.

As an example, a nano-emulsion encapsulating DiD prepared according to Example 4 was functionalised by a cyclopeptide (cRGD) capable of being fixed on the membranous receptors, the $\alpha_v\beta_3$ integrins. These integrins were overexpressed during the phenomenon of angiogenesis, namely the creation of new blood vessels notably accompanying most tumour growths.

Functionalization could be carried out before or after emulsification. An explanation is given hereinafter as to how to proceed to functionalise a cosurfactant before emulsification.

Preparation of a Targeting Peptide Functionalised by a Grafting Cosurfactant

A targeting cyclic peptide of the $\alpha_v\beta_3$ integrins overexpressed on the surface of endothelial cells, c(RGCf[ε-S-acetylthioacetylK sold by Ansynth Service BV (Netherlands) and called hereinafter cRGD possessing a protected thiol group in the form of a mercaptoacetic acid, was coupled with a grafting cosurfactant, distearoylphosphatidyethanolamine poly(ethylene glycol) 5000-maleimide (DSPE-PEG(5000)-maleimide sold by Avanti Polar Lipids Inc), the latter being mixed with cRGD with a 1:1 molar ratio in a sulphonic acid buffer solution of (4-(2-hydroxyethyl)-1-piperazineethane/ethylenediamine tetraacetic acid (HEPES/EDTA) with a 0.05 M hydroxylamine concentration. The solution was stirred slowly under a slight argon flow at room temperature for 4 hours, evaporated at low pressure and then redissolved in chloroform before the second step.

The functionalised nano-emulsion was then prepared following the protocol indicated in Example 2 except that 2% by weight of oil was replaced by the equivalent quantity of peptide prepared as indicated above.

A DiD doped nano-emulsion solution functionalised by cRGDs and, as a comparison, a non-functionalised DiD doped nano-emulsion were injected into mice carrying a tumour coming from Hek $\beta_3$ cells. These tumour cells were implanted in the back of female nude mice following a similar protocol as that described above.

A comparison of the development of the ratio of the tumour on the skin of mice treated by a nano-emulsion functionalised by cRGD to those having received a non-functionalised nano-emulsion demonstrated preferred accumulation of nano-particles functionalised by cRGD in the tumour. It demonstrated active targeting for the vectorization of the molecules concerned.

Thus, the nano-emulsion according to the invention constitutes a formulation of therapeutic agents capable of permitting more targeted administration, thus contributing to a reduction in the dose administered and, on account of this, the duration and undesirable side-effects of the treatment.

In addition, it was found that the load of therapeutic agent hardly altered the properties of the nano-emulsions prepared as regards the size of the dispersed phase, the nature of the interface and its load, the main factors acting in their in vivo biodistribution. Finally, nano-emulsions encapsulating active ingredients such as paclitaxel or photosensitizers accumulate in a passive manner in tumours, it being possible for this accumulation to be reinforced by active targeting by grafting a biological ligand such as for example cRGD.

The nano-emulsions provided according to the invention thus constitute an effective means for vectorizing, in a passive or active manner, therapeutic agents towards tumours and therefore constitute a valuable tool for improving the diagnosis and treatment of diseases such as cancer, notably by chemotherapy or phototherapy route.

Example 6

Highlighting Stability of the Nano-Emulsion

The experiments below were carried out in order to demonstrate the stability conferred to the nano-emulsions by the solubilising lipid.

Example 6A: Highlighting the High Inner Viscosity of the Droplets by Way of NMR

A nano-emulsion comprising 255 mg of Suppocire® NC (Gattefossé) (solubilising lipid), 85 mg of soybean oil (Sigma Aldrich) (oil), 345 mg of Myrj52® (ICI Americas Inc) (cosurfactant), 65 mg of Lipoid® s75 (lecithin, amphiphilic lipid) and a phosphate buffer (PBS) was prepared in accordance with the protocol of Example 1.

The nano-emulsion was analysed at 10° C. and at 60° C. by nuclear magnetic resonance of the proton. The peaks associated with the core components of the droplets of the nano-emulsion (oil/solubilising lipid and amphiphilic lipid) (0.9; 1.5; 1.6; 2.0; 2.2; 4.1; 4.2 ppm) observed within the $^1$H NMR spectra were enlarged compared with the reference (0 ppm 4,4-dimethyl-4-silapentane-1-sulphonic acid (DSS)), especially when the temperature was low, thus highlighting the high inner viscosity of the droplets. The peaks associated with the cosurfactant Myrj53® (3.7 ppm) did not exhibit any enlargement which indicates that the cosurfactant remained at the surface of the droplets, the polyoxyethylene chains being solubilised in the aqueous buffer (FIG. 7).

Example 6B: Highlighting the Absence of Crystallisation in the Droplets by Way of Differential Scanning Calorimetry A nano-emulsion comprising 150 mg of Suppocire® NC (Gattefossé) (solubilising lipid), 50 mg of soybean oil (Sigma Aldrich) (oil), 228 mg of Myrj53® (ICI Americas Inc) (cosurfactant), 100 mg of Lipoid® s75 (lecithin, amphiphilic lipid) and a phosphate buffer (PBS) was prepared in accordance with the protocol of Example 1.

The thermograms obtained by differential scanning calorimetry analysis of the nano-emulsion after preparation and after 4 months of storage at room temperature show that no fusion peak was observed after production, nor after storage at room temperature over 4 months, which indicates that the droplets were not crystallised (FIG. 8).

Example 6C: Revealing the Influence of the Composition of Nano-Emulsions on their Physical Stability Three nano-emulsions comprising 228 mg of Myrj53® (ICI Americas Inc) (co-surfactant), 100 mg of Lipoid® s75 (lecithin, amphiphilic lipid), 1600 µL of phosphate buffer (PBS), Suppocire® NC (Gattefossé) (solubilising lipid) and soybean oil (Sigma Aldrich) (oil) in the amounts indicated in Table 6 were prepared in accordance with the protocol of Example 1.

TABLE 6

| | Amounts of Suppocire ® NC and soybean oil in the nano-emulsions | | |
|---|---|---|---|
| Nano-emulsion | NC0 | NC50 | NC100 |
| Suppocire ® NC | 0 | 100 mg | 200 mg |
| Soybean oil | 200 mg | 100 mg | 0 |

A test of accelerated stability at 40° C. was carried out on the three nano-emulsions obtained. Monitoring the size/polydispersity of the nano-emulsions over time made it possible to highlight the stabilising effect of the solubilising lipid. Whereas the size of the nano-emulsions containing no solubilising lipid increased considerably after almost 170 days at 40° C., the nano-emulsions containing solubilising lipid exhibited no significant change in droplet size (FIG. 9). The results show that adding solubilising lipid to the composition of the nano-emulsions confers better physical stability to the droplets and to the nano-emulsion.

The invention claimed is:
1. Therapeutic agent formulation in the form of a stable nano-emulsion, comprising a continuous aqueous phase and at least one dispersed oily phase, wherein the surface of the dispersed phase has a zeta potential in a range of from more than −20 mV to less than 20 mV, wherein the aqueous phase comprises a polyalkoxylated cosurfactant comprising at least one chain composed of ethylene oxide units or ethylene oxide and propylene oxide units, wherein the oily phase also comprises (i) a therapeutic agent, and (ii) at least one phospholipid and at least one solubilising lipid consisting of a mixture of saturated fatty acid glycerides comprising:

0% to 20% by weight C8 fatty acids
0% to 20% by weight C10 fatty acids,
10% to 70% by weight C12 fatty acids,
5% to 30% by weight C14 fatty acids,
5% to 30% by weight C16 fatty acids, and
5% to 30% by weight C18 fatty acids, and wherein the dispersed oily phase has an average droplet size of from 10 to 200 nm, so that the therapeutic agent formulation exhibits colloidal stability during storage over a period of at least about 170 days at 40° C. and stealthy character upon administration.

2. Therapeutic agent formulation according to claim 1, wherein the oily phase further comprises at least one oil.

3. Therapeutic agent formulation according to claim 2, wherein the oil has a hydrophilic-lipophilic balance (HLB) of between 3 and 6.

4. Therapeutic agent formulation according to claim 1, wherein the cosurfactant is selected from the conjugated compounds polyethylene glycol/phosphatidylethanolamine (PEG-PE), fatty acid and polyethylene glycol ethers, fatty acid and polyethylene glycol esters, and ethylene oxide and propylene oxide block copolymers.

5. Therapeutic agent formulation according to claim 1, wherein the therapeutic agent is a pharmaceutical ingredient.

6. Therapeutic agent formulation according to claim 1, wherein the therapeutic agent is a photosensitizer.

7. Therapeutic agent formulation according to claim 1, characterised in that it is functionalised.

8. Method for preparing a therapeutic agent formulation in the form of a nano-emulsion comprising at least one continuous aqueous phase and at least one dispersed oily phase, said method comprising the steps of:

(i) preparing the oily phase comprising the therapeutic agent, a phospholipid and at least one solubilising lipid consisting of a mixture of saturated fatty acid glycerides comprising:

0% to 20% by weight C8 fatty acids
0% to 20% by weight C10 fatty acids,
10% to 70% by weight C12 fatty acids,
5% to 30% by weight C14 fatty acids,
5% to 30% by weight C16 fatty acids, and
5% to 30% by weight C18 fatty acids;

(ii) preparing an aqueous phase comprising a polyalkoxylated cosurfactant comprising at least one chain composed of ethylene oxide units or ethylene oxide and propylene oxide units;

(iii) dispersing the oily phase in the aqueous phase under the effect of sufficient shear force to form a nano-emulsion; and (iv) recovering the nano-emulsion thus formed, wherein the nano-emulsion is a therapeutic agent formulation according to claim 1.

9. Preparation method according to claim 8, wherein the shear force effect is produced by sonication.

10. Preparation method according to claim 8, wherein the oily phase is prepared by placing all or some of the constituents in solution in an appropriate solvent and subsequently evaporating the solvent.

11. Therapeutic treatment method comprising administration of an effective therapeutic amount of the formulation according to claim 1 to a mammal in need, thereof.

12. Therapeutic agent formulation according to claim 1, wherein the polyalkoxylated cosurfactant of the aqueous phase is the only polyalkoxylated cosurfactant in the therapeutic agent formulation.

13. Preparation method according to claim 8, wherein the polyalkoxylated cosurfactant of the aqueous phase is the only polyalkoxylated cosurfactant in the therapeutic agent formulation.

* * * * *